United States Patent [19]

Philpot, Jr.

[11] Patent Number: 4,461,830

[45] Date of Patent: Jul. 24, 1984

[54] SERUM FIBRINOGEN VISCOSITY IN CLINICAL MEDICINE

[76] Inventor: Van B. Philpot, Jr., P.O. Box 312, Houston, Miss. 38851

[21] Appl. No.: 459,494

[22] Filed: Jan. 20, 1983

[51] Int. Cl.³ .................. G01N 33/48; G01N 33/68; G01N 33/86; G01N 33/96

[52] U.S. Cl. ........................................ 435/13; 73/55; 128/637; 436/69

[58] Field of Search .............. 435/13; 436/69; 422/73; 128/637; 73/55

[56] References Cited

U.S. PATENT DOCUMENTS

| | | | |
|---|---|---|---|
| 3,342,063 | 9/1967 | Smythe | 73/55 |
| 3,861,197 | 1/1975 | Adler | 436/69 X |
| 3,911,728 | 10/1975 | Fixot | 73/55 |
| 3,960,669 | 6/1976 | Innerfield | 435/13 |
| 3,990,947 | 11/1976 | Butler | 435/13 |
| 3,999,538 | 12/1976 | Philpot | 128/637 |
| 4,081,242 | 3/1978 | Girolami | 422/73 X |
| 4,083,363 | 4/1978 | Philpot | 128/637 |
| 4,165,632 | 8/1979 | Weber | 73/55 |
| 4,300,551 | 11/1981 | Kinney | 128/637 X |

OTHER PUBLICATIONS

Chemical Abstracts, 91: 72753z, (1979).
Chemical Abstracts, 95: 59360y, (1981).

Primary Examiner—Sidney Marantz
Attorney, Agent, or Firm—Cushman, Darby & Cushman

[57] ABSTRACT

A solution of purified, standardized fibrinogen is added to a sample of coagulant-free serum from subject, and the viscosity of the resulting solution is measured. The measurement may be related to diagnosing an abnormal body condition, such as schizophrenia or selecting the optimum chemotherapeutic agent in treatment.

16 Claims, 1 Drawing Figure

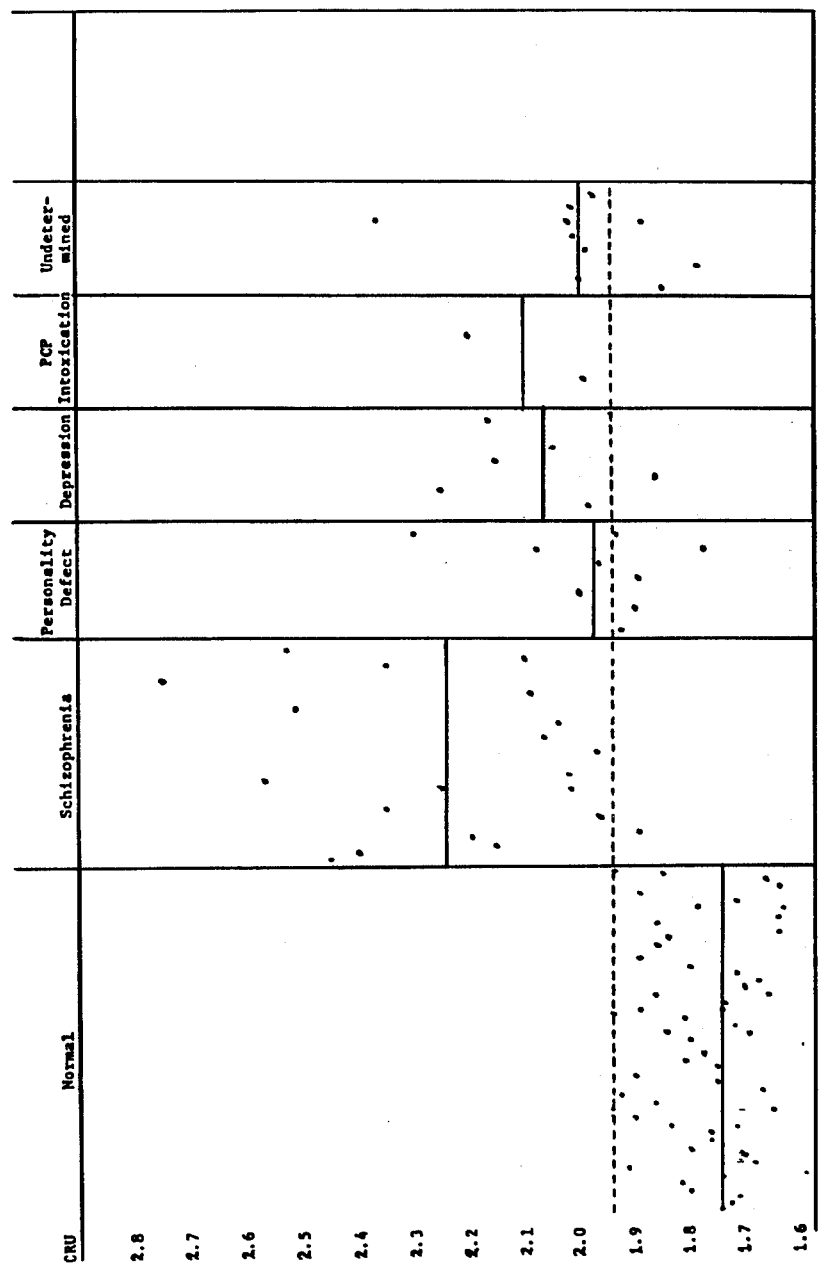

SERUM FIBRINOGEN VISCOSITY IN CLINICAL MEDICINE

BACKGROUND OF THE INVENTION

The measurement of the flow of blood through a device to measure blood viscosity, termed rheocohesion in the art, is a valuable diagnostic procedure. However, problems in obtaining a correct rheocohesion value include: improper venipuncture causing artifacts in the readings so obtained; special equipment is needed to accurately measure the rate of flow of blood through a hypodermic needle inserted directly into the blood vessel of a patient under study while maintaining controlled conditions of standard pressure, temperature and time; whole blood rheocohesion is an indirect measurement, and artifacts such as the hematocrit and total serum protein must be considered.

The measurement of whole blood rheocohesion is described in my earlier U.S. Pat. No. 3,999,538 and the apparatus described in my U.S. Pat. No. 4,083,363.

It would be convenient to obtain a single blood sample for numerous blood testing purposes from the patient using conventional syringe and/or vacutainer without specialized equipment of the type referred to above.

I have now found, and hereby disclose, a procedure for measuring the change in viscosity of fibrinogen using the serum of a patient, or serum fibrinogen viscosity, and of correlating the viscosity values obtained with whole blood rheocohesion. Serum fibrinogen viscosity values are useful in diagnosis of numerous abnormal conditions, for instance trauma as manifested by myocardial infarction and the possible need for anticoagulant therapy, and the potential for a pulmonary embolus following major surgery.

Another significant application for serum fibrinogen viscosity is in the diagnosis and selective therapy of abnormal conditions, for example schizophrenia, and distinguishing schizophrenia from other psychiatric conditions.

Plasma is the clear liquid when whole blood is placed in an anticoagulant and the cellular elements of the blood settle to the bottom. Plasma is routinely obtained in blood banks by physical separation, i.e., centrifuge, to separate the cellular elements by gravity, from the clear, straw-colored liquid. The serum obtained for use in the present invention is withdrawing a blood sample from the patient and placed in a container without an anticoagulant, centrifuging to separate the cellular elements from the clear liquid. Serum thus obtained is free from anti-coagulants. Without an anticoagulant the blood fibrinogen is converted into fibrin, a three-dimensional gelatin-like network of fibers. As such the fibrin network is separated by the centrifuge, or spun down, with the red cells leaving the clear liquid at the top; the serum thus treated, contains no fibrinogen. Serum, then, is the same as plasma minus fibrinogen.

It is important that no anticoagulant be used in the procedure. The object of this procedure is to omit the patient's fibrinogen and to use the serum to analyze factors that influence purified, standardized fibrinogen, as discussed in more detail below.

In conventional rheology, the term "whole blood viscosity" refers primarily to values obtained by placing anticoagulated blood in rotational viscometers at varying shear rates. Since the results reported in my application are quite different from those of conventional viscometers and since entirely different phenomena are measured, the term rheocohesion is used below in place of viscosity.

Determination of Whole Blood Rheocohesion

The rheocohesive meter preferred for use in the present invention consists of a 10.0 ml syringe attached by a three-way stop cock and connecting tubing to a compound pressure gauge as shown, for example, in my earlier U.S. Pat. Nos. 3,999,538 and 4,083,363, disclosures of which are hereby incorporated by reference. In the preferred embodiment the gauge is protected from contamination by blood is a Gelman filter Acrodisc C R. A ⅜ in. 21 gauge needle attached to a 6-inch butterfly tubing is used for the venipuncture.

A blood pressure cuff is placed around the forearm and inflated to 30 mm Hg. Using sterile precautions a venipuncture is performed in the antecubital vein and blood is allowed to flow into the system giving a reading on the positive pressure side of the gauge. When the flow of blood becomes stabilized, this reading is recorded as the venous pressure. Blood is then withdrawn into the syringe at a standard negative pressure for a specified period of time (usually 80 mm mercury for 15 seconds). The negative pressure is then added to the venous pressure to give the combined hydrostatic pressure forcing blood into the syringe.

The entire instrument, including the butterfly needle and syringe, is calibrated using distilled water at 37° C. as a standard. A graph is constructed showing the amount of distilled water withdrawn into the syringe at varying negative pressures for the standard period of time used in this procedure. From the graph one determines the amount of distilled water then can be drawn into the system using the total hydrostatic pressure of withdrawing blood in a test situation. The volume of blood withdrawn under a test situation is then divided into the volume of distilled water withdrawn and the result is expressed in total rheocohesive units (TRU).

The total rheocohesiveness of blood is determined to a large extent by the hematocrit and it was considered advisable in psychiatric patients to exclude the hematocrit as a variable. Four hundred fifty ml of blood was withdrawn from a normal volunteer in a blood bank and placed in a plastic bag containing 63 ml of CPDA-1 soln. as an anticoagulant. The plasma was separated from the cells and reconstituted at levels of 10%, 20%, 30%, 40%, 50%, 60%, and 70% hematocrits. Rheocohesion values were determined and a relationship determined when rheocohesive units are plotted against hematocrit. Between the values of 30 to 60% hematocrit the curve is relatively straight and the rheocohesiveness of blood increases 0.043 units for each 1.0% hematocrit. Using this factor corrections can be made to a level of 40% hematocrit thus eliminating the hematocrit as a variable in the final result. These results are reported as corrected rheocohesive units (CRU). The TRU of males is greater than females while there is no significant difference in the CRU of males and females.

Other instruments for measuring serum and plasma viscometers may be used.

Measuring Serum Fibrinogen Viscosity

A simple test for measuring serum fibrinogen viscosity (SFV) is as follows: A solution of purified fibrinogen is prepared daily at a concentration of approximately 2.5 mg per ml. Seven ml of this solution is placed into each of two test tubes. To one of the test tubes, 1.0 ml of 0.9% saline solution is added and to the second test tube, 1.0 ml of the patient's serum is added. The viscosity of the fibrinogen solution is determined using a viscometer and the serum-fibrinogen mixture is allowed to incubate for one hour. The viscosity of the serum-fibrinogen solution is then determined. Normal serum under these circumstances will give no increase in the viscosity of the fibrinogen solution. The serum of schizophrenic patients, however, is biologically abnormal and will give an increase in the viscosity of this solution.

It has been determined that the whole blood viscosity of patients with schizophrenia is elevated prior to treatment yet following successful treatment, the viscosity of this blood goes down. While not wishing to be bound to any particular theory, it is believed that the effect that the effective psychotropic drug has on the schizophrenic patient is to neutralize the factor in the serum that is acting on the protein fibrinogen. The following data will demonstrate a factor in schizophrenic serum that increases the viscosity of the fibrinogen.

It is recognized in the art that blood serum of schizophrenic patients is biochemically unique and differs from the blood serum of the normal population. A possible explanation for the increase in whole blood rheocohesion in psychiatric patients is the ability of serum of all patients with above 2.0 corrective rheocohesive serum unit (CRU) to increase the rheocohesion of purified fibrinogen; this is believed to occur in the living patient. Rheocohesion may be related to the state of polymerization of the fibrinogen is related to enzymes and their activators and inhibitors which are extremely labile; see MacFarlane et al "Observations on Fibrinolysis: Spontaneous Activity Associated With Surgical Operations, etc. *Lancet* 2:862 (1946). Tooney and Cohen have reported aggregation of fibrinogen without coagulation by such enzymes as extract of *Pseudomonas aerugenosa;* see *J. Molecular Biol.,* pp. 110-363 (1977). Such altered fibrinogen can produce a clot when exposed to thrombin.

Heath described a protein fraction from the serum of schizophrenia patients called taraxein which was found in a specific subfraction of schizophrenic gamma G immunoglobulin. When introduced into monkeys, taraxein caused abnormal EEG changes and catatonic behavior; see *Amer. J. Psychiat.* 114:14 (1957) and *Dis. Nervous Systems* 31:391 (1970). When introduced into human volunteers, taraxein produced signs and symptoms chracteristic of the schizophrenic patient. Bergen described a biologically active substance in the alpha 2 globulin fraction of the plasma of schizophrenic patients which was not found in the plasma of normal volunteers *Res Commun. in Chem. Path and Pharmacol* 1:403 (1970). Solntseva reported that application of serum from schizophrenia patients caused inhibition of unit activity of neurones from *Helix pomatia* while normal serum did not Zhurnal Nevropatologii i Psikiatrii imeni SS. Korsakova, 71:704. The possibility of one or more of these factors causing fibrinogen aggregation in vivo in schizophrenic patients cannot be excluded.

The specific procedure used in the following clinical studies was as follows: Purified bovine or human fibrinogen was reconstituted in 0.9% (normal) saline in a concentration of 2 to 3 mg per ml. One ml of serum from each of 10 normal volunteers and 14 psychiatric patients was added to 7.0 ml of the fibrinogen solution. Controls included 1.0 ml saline plus 7.0 ml fibrinogen and 1.0 ml serum plus 7.0 ml saline. All solutions were incubated for 1 hour at 37° C. and viscosity determinations performed on each using the blood viscosity determination device of U.S. Pat. No. 4,083,363. Results were reported in Table I, below, as positive or negative. If the test serum produced a 6% or greater increase in viscosity of the fibrinogen the result was reported as positive; if there was no significant increase in viscosity the result was reported as negative.

Normal volunteers included students, faculty, and technicians of a major medical school; ages ranged from 18 to 65 and representatives of caucasian, black, and Oriental races included.

The patients used in this study were hospitalized. The study was made in a double blind fashion. Rheocohesion studies were made by one investigator who did not know the diagnosis and the diagnoses were made by a clinical psychiatrist who did not know the rheocohesion values. Results were compiled at the end of the study. All psychiatric patients had a battery of other laboratory studies including complete blood count, urinalysis, serum total protein, albumin, calcium, inorganic phosphorous, glucose, blood urea nitrogen, uric acid, creatinine, total bilirubin, alkaline phosphatase, lactic dehydrogenase (LDH), glutamic oxaloacetic transaminase (SGOT), potassium, chlorides, and bicarbonate ($CO_2$).

The method for rheocohesion results are reported to the second decimal point for the sake of clarity as illustrated in the scattergram of the attached FIGURE. Elsewhere the values are reported to the first decimal point.

The scattergram of FIG. 1 reports whole blood rheocohesion in normal volunteers and psychiatric patients with median values represented as a solid line and a dashed line as the upper limit of normal. The scattergram shows that the corrected rheocohesive units of blood of 55 normal volunteers was 1.63–1.93 CRU. There was no significant difference between race, sex, or age. Only 10 of the 50 patients were within the normal range. Most of the patients were divided into 6 categories: schizophrenia, personality defect and drug abuse, depression, PCP intoxication, and psychosis undetermined. Of these, patients with schizophrenia had the highest mean value (2.23 CRU). Of 20 schizophrenic patients, only 1 was within the normal range and the highest CRU was 2.75. The majority, i.e., 5 of 9, patients with personality and drug abuse problems were within the normal range. Three of the remaining 4 were only slightly above normal.

Patients with depression and PCP intoxication showed moderate elevations of rheocohesion ranging from 2.0 to 2.3. Three patients with undetermined psychosis had normal values and 7 had CRU ranging from 1.96 to 2.36. For completion of the data, three patients not represented in FIG. 1 were carbon monoxide poisoning 2.01 CRU, organic brain syndrome (OBS) 2.18 CRU, and situational anxiety with suicide tendency 2.3 CRU.

Correlation of Whole Blood Rheocohesion to Serum Fibrinogen Viscosity (SFV)

Table I shows that patients with CRU greater than 2.0 caused a significant increase in the viscosity of purified fibrinogen and serum from patients with CRU of 2.0 or less did not. The increase in viscosity by abnormal sereum ranged from 6% to 30%. Controls showed no significant difference between the viscosity of serum alone from volunteers and patients with normal blood CRU values and those with markedly elevated values.

TABLE I

| | Serum Fibrinogen Viscosity (SVR) Compared with Whole Blood Viscosity | | | |
|---|---|---|---|---|
| | Patients | | Normals | |
| Diagnosis | Whole Blood CRU | FR* Test | Whole Blood CRU | FR* Test |
| Schizophrenia | 2.2 | + | 1.8 | − |
| Schizophrenia | 1.9 | − | 1.8 | − |
| Schizophrenia | 2.4 | + | 1.6 | − |
| Schizophrenia | 2.0 | − | 1.7 | − |
| Schizophrenia | 2.2 | + | 1.9 | − |
| Schizophrenia | 2.6 | + | 1.9 | − |
| Schizophrenia | 2.2 | + | 1.7 | − |
| Schizophrenia | 2.5 | + | 1.8 | − |
| Schizophrenia | 2.8 | + | 1.9 | − |
| Personality defect | 1.9 | − | 1.7 | − |
| Personality defect | 2.0 | − | | |
| Personality defect | 1.9 | − | | |
| Depression | 2.3 | + | | |

*+means 6% or greater increase in rheocohesion of fibrinogen by serum.
−means no increase.

Follow-up studies were done on ten patients 7 to 10 days after admission; see Table II, below. Initial blood samples were taken prior to commencing drug therapy in the institution. Nine of these patients showed a drop in whole blood CRU. One patient showed an increase in whole blood CRU and this patient failed to respond clinically to therapy after three weeks.

Laboratory studies revealed one patient with severe anemia who was deleted from the series. The remainder showed no significant abnormality in the laboratory procedures performed. Of particular significance is the absence of any abnormality of serum proteins or AG ratio.

TABLE II

| | Effect of Neuroleptic Drugs on Whole Blood Rheocohesion | | | |
|---|---|---|---|---|
| | | | Second test | |
| Diagnosis | Admission CRU | Treatment | Days of Admission | CRU |
| Schizophrenia | 2.5 | Stellazine | 7 | 1.8 |
| Schizophrenia | 2.4 | Prolixin | 7 | 1.9 |
| Schizophrenia | 2.2 | Prolixin | 7 | 2.7 |
| Depression | 2.0 | Navane | 10 | 1.9 |
| Schizophrenia | 2.2 | Navane | 7 | 2.1 |
| Schizophrenia | 2.6 | Prolixin | 8 | 2.1 |
| Schizophrenia | 2.0 | Prolixin | 7 | 1.8 |
| Schizophrenia | 2.2 | Stellazine | 8 | 1.9 |
| Schizophrenia | 2.1 | Haldol, Prolixin | 8 | 1.9 |
| OBS | 2.2 | Haldol | 7 | 1.9 |

Furthermore increased blood rheocohesion is not specific for any particular type of mental and emotional disorder since some patients in all categories had abnormally high values. The test may be of some value in screening for patients with personality and drug abuse problems since most patients in this category showed normal blood rheocohesion values while only 1 of 20 patients with schizophrenia had normal levels of CRU. Furthermore all patients with CRU levels greater than 2.4 were diagnosed as having schizophrenia. It is therefore very clear that studies on whole blood rheocohesion are more frequently and more strongly positive in schizophrenia than in other mental and emotional disorders.

The usefulness of blood rheocohesion studies as a biological marker for response to neuroleptic drugs is strongly suggested by the data reported in Table II. Nine of 10 patients showed a drop in whole blood rheocohesion. The only patient to show a rise in blood CRU showed no clinical response to treatment. Although follow-up studies were usually made 7–10 days after admission, a significant drop in blood CRU has been observed in 24–48 hours. The decrease in whole blood CRU usually precedes the clinical response.

The routine laboratory studies did not explain the phenomenon of increased whole blood rheocohesion in these psychiatric patients. Most of the routine studies were normal and the small number of abnormalities showed no correlation with whole blood rheocohesion. Volunteers who were anemic had elevated CRU and those with anemia were therefore deleted from the normal as well as patient population in this series.

Serum/Drug Effectiveness Testing

As demonstrated above, there is a correlation between schizophrenia and increased serum fibrinogen viscosity (and also whole blood rheocohesion). It has further been shown that psychotropic drugs reduce whole blood rheocohesion when the patient's condition improves and fails to do so when the patient's condition deteriorates. Since there is a correlation between whole blood rheocohesion and SFV it is expected that the psychotropic drugs would "neutralize" the SFV factor if a given drug is effective in the treatment of the patient. The SFV procedure thus lends itself to possible use as a simple in vitro method for determining the optimum drug for the patient involved on the day of admission.

A simple screening method is as follows:

(1) solutions of candidate drugs are prepared at concentrations as would be encountered in the blood stream of patients taking the customary and therapeutically effective dosage rates;

(2) each drug solution so prepared is added to samples of the patient's serum in an approximately 1:1 ratio;

(3) the SFV is determined, as described above, using 1 ml of the 1:1 drug:serum mixture in place of the 1 ml of serum.

If the drug is effective for the patient, it is expected that the SFV factor would be neutralized giving a conversion from a positive test with the serum alone to a negative test with the serum/drug mixture.

Controls will include a 1:1 mixture of test serum and saline and a 1:1 mixture of drug solution plus saline.

Using this procedure one is able to obtain a blood sample upon admission, carry out the comparisons and observations noted above, and determine the optimum chemotherapy for the patient's condition.

Although specific emphasis has been given to schizophrenia and the selective diagnosis of same, other abnormal conditions, such as neurosis and psychosis, may be susceptible to this procedure, including tissue trauma, post-operative states, myocardial infarction and chronic pain.

What is claimed is:

1. A method of diagnosing an abnormal body condition of a subject animal comprising the successive steps of:

(1) securing a sample of coagulant-free serum from the patient under study;

(2) adding a solution of purified, standardized fibrinogen to a sample of the serum of step (1) and allowing the resulting mixture to incubate;

(3) measuring the viscosity of the mixture of step (2) to determine the serum fibrinogen viscosity;

(4) comparing the serum fibrinogen viscosity value measured in step (3) with a predetermined serum fibrinogen viscosity of a normal population of patients when treated under conditions similar to those of step (2); and (5) diagnosing an abnormal body condition of said subject in accordance with the values compared in step (4).

2. A method of selecting the optimum chemotherapeutic agent in the treatment of an abnormal body condition in a subject animal comprising the successive steps of:

(1) securing a sample of coagulant-free serum from the animal under study;

(2) mixing a portion of the serum of step (1) with a solution of a candidate chemotherapeutic agent in a concentration approximating at least the minimum effective therapeutic concentration in the blood of a subject receiving the candidate chemotherapeutic agent at a predetermined dosage level;

(3) repeating step (2) with a plurality of candidate chemotherapeutic agents;

(4) adding a solution of purified, standardized fibrinogen to each of the serum/chemotherapeutic agent mixtures prepared in step (3) and allowing each of the resulting mixtures to incubate;

(5) measuring the viscosity of each of the mixtures prepared in step (4) to determine the serum fibrinogen viscosity;

(6) comparing the serum fibrinogen viscosity values measured in step (5) with a predetermined averaged serum fibrinogen viscosity of a normal population of patients when treated under conditions similar to those of step (4); and (7) determining the candidate chemotherapeutic agent that effectively reduces the patient's serum fibrinogen viscosity to approximate the predetermined serum fibrinogen viscosity of the normal population as compared in step (6).

3. The method of claim 2 wherein the incubation of steps (4) and (6) is for a period of about 15 minutes to about 24 hours at about 37° C.

4. The method of claim 3 wherein the incubation period is about one hour.

5. The method of claim 2 wherein the ratio of serum to chemotherapeutic agent solution in step (4) is about 1:1.

6. The method of claim 2 wherein the concentration of purified and standardized fibrinogen in the solution of step (4) is about 1 to about 5 mg per ml. of solution.

7. The method of claim 6 wherein the concentration of fibrinogen is about 2 to about 3 mg/ml.

8. A method of diagnosing schizophrenia in a subject patient and distinguishing schizophrenia from other psychiatric disorders, said method comprising the successive steps of:

(1) securing a sample of coagulant-free serum from the patient under study;

(2) adding a solution of purified, standardized fibrinogen to a sample of the serum of step (1) and allowing the resulting mixture to incubate;

(3) measuring the viscosity of the mixture prepared in step (2) to determine the serum fibrinogen viscosity;

(4) comparing the serum fibrinogen viscosity value measured in step (3) with a predetermined serum fibrinogen viscosity of a normal population of patients when treated under conditions similar to those of step (2); and (5) selectively diagnosing schizophrenia from among other psychiatric disorders.

9. A method of selecting the optimum chemotherapeutic agent in the treatment of schizophrenia comprising the successive steps of:

(1) securing a sample of coagulant-free serum from the patient under study;

(2) mixing a portion of the serum of step (1) with a solution of a candidate chemotherapeutic agent in a concentration approximating at least the minimum effective therapeutic concentration in the blood of a person receiving the candidate chemotherapeutic agent at a predetermined dosage level;

(3) repeating step (2) with a plurality of candidate chemotherapeutic agents;

(4) adding a solution of purified, standardized fibrinogen to each of the serum/chemotherapeutic agent mixtures prepared in step (3) and allowing each of the resulting mixtures to incubate;

(5) measuring the viscosity of each of the mixtures prepared in step (4) to determine the serum fibrinogen viscosity;

(6) comparing the serum fibrinogen viscosity values measured in step (5) with a predetermined serum fibrinogen viscosity of a normal population of patients when treated under conditions similar to step (4); and (7) determining the candidate chemotherapeutic agent that effectively reduces the patient's serum fibrinogen viscosity to approximate the predetermined serum fibrinogen viscosity of the normal population as compared in step (6).

10. The method of claim 9 wherein the incubation of steps (4) and (6) is for a period of about 15 minutes to about 24 hours at about 37° C.

11. The method of claim 10 wherein the incubation period is about one hour.

12. The method of claim 9 wherein the ratio of serum to chemotherapeutic agent solution in step (4) is about 1:1.

13. The method of claim 9 wherein the concentration of purified and standardized fibrinogen in the solution of step (4) is about 1 to about 5 mg per ml. of solution.

14. The method of claim 13 wherein the concentration of fibrinogen is about 2 to about 3 mg/ml.

15. The method of claim 9 wherein the serum fibrinogen viscosity is measured in step (5) by withdrawing serum;

(a) through an opening of a predetermined effective dimension;

(b) under conditions of a predetermined substantially constant negative pressure so as to establish a corresponding predetermined substantially constant fluid pressure drop across said opening;

(c) for a predetermined period of time and until a variable volume sample of serum has been withdrawn; and (d) measuring the volume of serum so withdrawn which serum volume is inversely proportional to the viscosity of the serum.

16. The method of claim 9 wherein the serum fibrinogen viscosity is measured by step (5) by withdrawing said serum;
   (a) through an opening of a predetermined effective dimension;
   (b) under conditions of a predetermined substantially constant negative pressure so as to establish a corresponding predetermined substantially constant fluid pressure drop across said opening; and
   (c) for a variable amount of time to withdraw a predetermined volume of serum; and
   (d) measuring the time required to withdraw the predetermined volume of serum which measured withdrawal time is directly proportional to the viscosity of the serum.

* * * * *